United States Patent [19]

Veloso

[11] 3,947,486

[45] Mar. 30, 1976

[54] HYDROGENATION CATALYST
[75] Inventor: Alberto E. Veloso, Quezon, Philippines
[73] Assignee: Internationale Erfinder-und Patentanstalt, Vaduz, Liechtenstein
[22] Filed: Apr. 12, 1974
[21] Appl. No.: 460,591

Related U.S. Application Data
[62] Division of Ser. No. 82,421, Oct. 20, 1970, Pat. No. 3,819,724.

[52] U.S. Cl. ............................................. 252/465
[51] Int. Cl.$^2$ .................... B01J 21/04; B01J 23/64
[58] Field of Search ................................... 252/465

[56] References Cited
UNITED STATES PATENTS
2,840,619    6/1958    Mason et al. .................... 252/465 X Primary Examiner—W. J. Shine
Attorney, Agent, or Firm—Russell & Nields

[57] ABSTRACT

A process for the preparation of alcohols from purified carbon, including the step of hydrogenating the carbon at high temperature and pressure in a catalytic reactor in a dispersion with naphthalene and in the presence of a catalyst comprising nickel, ruthenium, aluminum and cobalt molybdate, and the step of oxidizing the resulting paraffins by contact with steam at high temperature and pressure in a catalytic reactor in the presence of a catalyst comprising a mixture of silica and copper and the oxides of zinc, chromium and boron. The catalysts are suspended in a ceramic concrete aggregate, extending the length of the reactors and in the form of a cylindrical reactor liner and a smaller, concentric ceramic cylinder therewithin. The second step is performed in two reactors in series.

1 Claim, 1 Drawing Figure

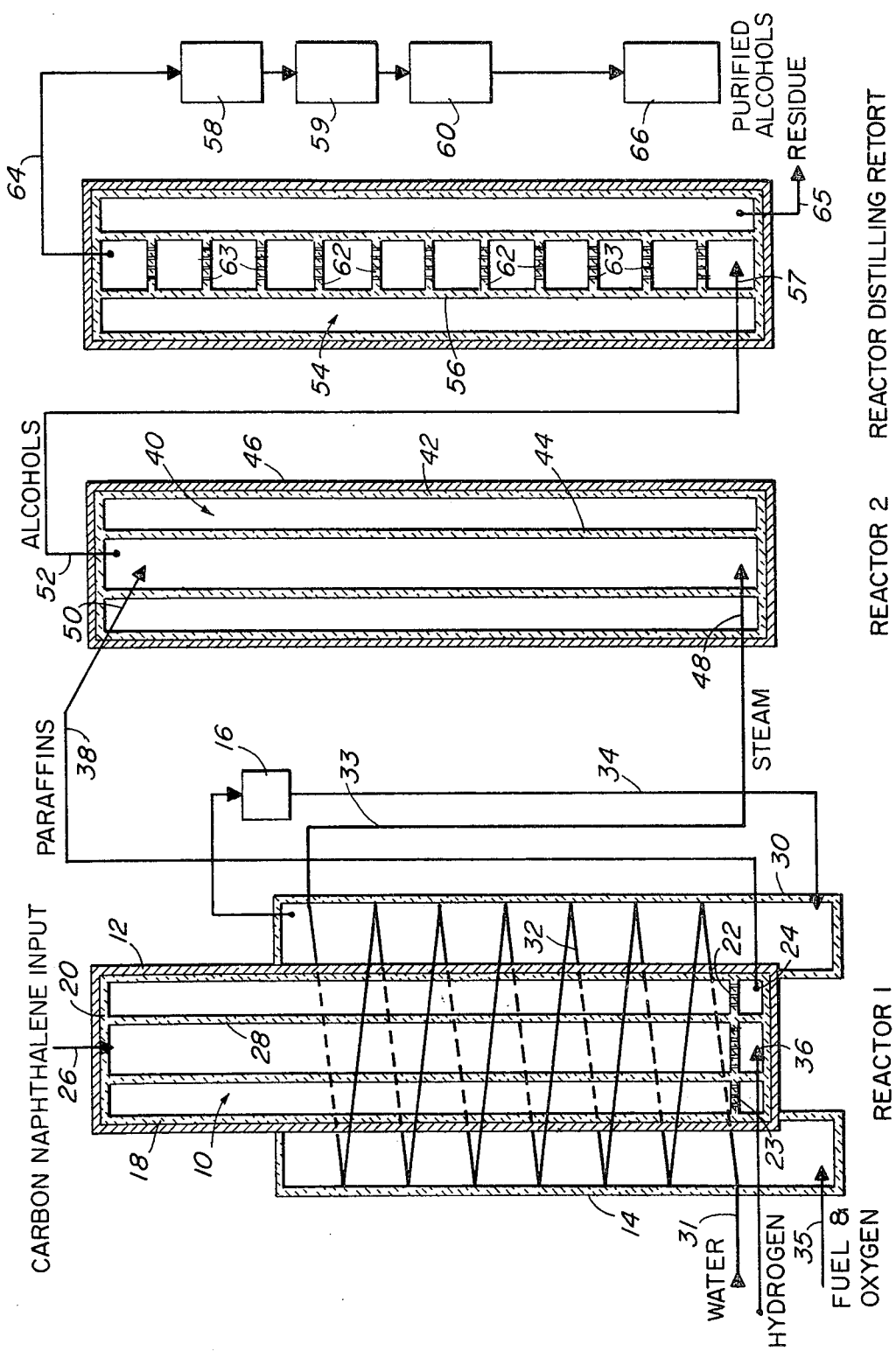

3,947,486

HYDROGENATION CATALYST

This is a division of application Ser. No. 82,421 filed Oct. 20, 1970 now U.S. Pat. No. 3,819,724.

BACKGROUND OF THE INVENTION

The field of this invention is the preparation of alcohols by the two-step process of hydrogenating purified carbon to form a mixture of paraffins, and of oxidizing the paraffins to form their respective alcohols.

Alcohols have been proposed for use as motor fuels. Their primary advantage is that their exhaust products contain little or no pollutants, being substantially completely carbon dioxide and water. There is, however, no practical, large-scale process suitable for the preparation of alcohol that is competitive with the traditional sources of motor fuel. It is, therefore, the major objective of this invention to provide a process for the preparation of alcohols of sufficient quantity to be competitive with conventional petroleum-based motor fuels.

In the present process, alcohols are synthesized from coal, or another source of purified carbon. The purified carbon may be obtained from charcoal, coal or a vegetable carbon source, for example, by the process described in my patent application, Ser. No. 82,549, filed Oct. 20, 1970, now U.S. Pat. No. 3,689,233, entitled Process For The Manufacture Of Hard Ashless Charcoal Briquettes. Said purified carbon, as disclosed at column 4 lines 30–33 of said patent, is material which is substantially pure and ashless, comprising essentially 99.75 percent carbon. It is then a further objective to provide a process for the preparation of alcohols from a readily available source of carbon, such as coal.

The well-known Bergius process converted powdered coal and heavy oil to hydrocarbons, by catalytic hydrogenation. It is a further objective of this invention to provide an improved method of hydrogenating a carbon source, as well as to oxidize the resulting hydrocarbons to alcohols.

SUMMARY OF THE INVENTION

In the present process, purified carbon is hydrogenated in the presence of a catalyst compound of about 15–20 percent nickel, 15–20 percent cobalt molybdate, 15–20 percent ruthenium, and 45–55 percent aluminum, at a temperature of about 500°–1500°C. and a pressure of about 100–3000 atm. The resulting hydrocarbons, primarily paraffins are oxidized in a second catalytic reactor with steam in the presence of a catalyst comprised of about 5–10 percent zinc oxide, 2–5 percent copper, 20–25 percent chromium oxide, 20–25 percent silica, 20–25 percent potassium oxide and 20–25 percent boric oxide, at about 300°–550°C and 400–500 atm., to form the corresponding alcohols.

The two reactors contain two concentric, porous ceramic cylinders impregnated with the catalyst composition. The hydrogenation reactor is heated by an external, concentric furnace, which also serves to heat the steam employed in the oxidation reactor. A third reactor-distilling retort, which serves to complete the oxidation to alcohols and to distill the product, is of special construction.

BRIEF DESCRIPTION OF THE DRAWING

The drawing shows schematically the equipment suitable for carrying out the present process, including a hydrogenation reactor, an oxidation reactor, and a reactor-distilling retort.

DETAILED DESCRIPTION OF THE INVENTION

The raw material of the present invention is ashless or purified carbon, which may be obtained by any suitable process, such as the method of preparing ashless vegetable black disclosed in my concurrently filed application, Ser. No. 82,549. In the first step of the process, the purified carbon is catalytically hydrogenated at high temperature and pressure, to form hydrocarbons, principally $C_1$–$C_{10}$ alkanes. The resulting hydrocarbons are next oxidized catalytically by steam to form the corresponding alcohols, also at high temperature and pressure.

The hydrogenation reactor is specially constructed, having the catalyst impregnated in porous, concentric ceramic cylinders, contained in a steel shell. The purified carbon is combined with naphthalene, comprising about 3–10 percent by weight of the charge, and charged into the reactor, in combination with part of the catalyst, comprising about 2 percent of the charge. A porous, catalyst-impregnated ceramic strainer is provided at the bottom to hold the charge and to distribute the hydrogen, charged into the bottom of the reactor. Temperature and pressure are raised gradually to about 500°C. and 1000 atm, or higher depending upon the desired end product and reaction time. Residence time during hydrogenation is about 2–3 hours. The hydrogenation catalyst comprises about 15–20 percent nickel, 15–20 percent cobalt molybdate, 15–20 percent ruthenium and 45–55 percent aluminum.

The hydrogenated products are charged, still under pressure, to the top of an oxidation reactor, which may be constructed in the same manner as the first reactor. Steam is charged to the bottom of the second reactor. Again, the catalyst, which comprises about 5–10 percent zinc oxide, 2–5 percent copper, 20–25 percent chromium oxide, 20–25 percent silica, 20–25 percent potassium oxide and 20–25 percent boric oxide, is impregnated into porous, ceramic material. The oxidation reaction proceeds at about 300°–550° C. and 400–500 atm.

The oxidation product is preferably charged into a reactor-distilling retort, also containing the same oxidation catalyst impregnated in porous ceramic material. There the oxidation reaction is completed, and the product alcohol is distilled and purified. In order to facilitate the distillation, the interior ceramic cylinder is provided with a series of perforated horizontal plates up the length of the retort. The product alcohols are removed from the top of the reactor-retort, condensed and recovered.

The catalysts employed in the present process may be reactivated, as the need arises, by heating in the absence of hydrocarbons to 1500°–1600°C.

The invention will be better understood with reference to the attached drawing, which shows equipment suitable for carrying out the present process, and preferred construction details of the reactors employed.

A mixture of 3–10 percent naphthalene and purified carbon is ground to very fine powder and the whole mass is further mixed with a combined catalyst (1 part nickel, 1 part cobalt molybdate, 1 part ruthenium, and 3 parts aluminum) which comprises about 2 percent of the whole mass. The whole mixed mass is then charged into the hydrogenation reactor 10. The reactor chamber 10 is made of 1½ inch steel cylinder 12, 6 feet in diameter and 24 feet long. The vertical reactor is supported with heavy steel framework (not shown) and coated with a mixture of manganese dioxide, potters clay, pulverized brick, and dolomite, and lined with refractory bricks. About two-thirds of the length of the reactor is surrounded by furnace 14, which is equipped with a device 16 to trap all the combustion products as the furnace 14 is being fired. The reactor chamber 10 is lined with a ceramic layer 18. The ceramic layer is porous and contains impregnated catalyst. It is composed of 3 parts granulated firebricks, 3 parts washed silica, 1 part slaked lime, 1 part portland cement, and to 5 percent of the whole mass is added potassium oxide. The whole mass is mixed with enough amount of water to compose a concrete aggregate, and the concrete aggregate is dosed with a catalytic mixture of 1 part nickel, 1 part cobalt molybdate, 1 part ruthenium, and 3 parts metallic aluminum powder. The catalyst constitutes about 3–5 percent of the whole concrete aggregate. However, before the catalyst mixture is introduced or mixed with the concrete aggregate the molders for the ceramic lining must be made ready, for upon mixing the catalyst mixture, the concrete aggregate will form a highly porous (foamy) dough. When the ceramic has properly set, it is dipped into a solution of 10–20 percent nickel acetate, after which the ceramic is dried. When completely dryed, it is fired to 1,500°C. In lining the ceramic, a mortar made of 1 part lime, 1 part portland cement, 3 parts dolomite (calcined), and 5 parts washed silica is employed. When the whole lining construction 18 has set, it is again fired or heated to about 1,600°C. The top of the reactor is also lined with the same ceramic construction 20, and cured to activate the catalyst mixture. At the bottom of the reactor 10, a strainer 22 of the same ceramic construction, containing multiple perforations 23, is incorporated. The reactor 10 is provided with a withdrawal outlet 24 at the bottom and a mechanical charging means 26 at the top. The reactor 10 is equipped with thermometer and pressure gauge and an agitator-grinder (not shown) to emulsify the liquidised carbon in the strainer cylinder 22. Extending upwardly from strainer 22 and concentric to liner 18 is a ceramic cylinder 28 of about 6 inch thick and 4 feet diameter with structural reinforcement made of nickel-plated aluminum bars (not shown), extending the length of the interior of the reactor steel cylinder. The ceramic cylinder 28 also contains the mixed catalyst, so its construction and composition are similar to the ceramics lining 18 of the steel cylinder reactor 10. This cylinder serves a dual purpose, first as a catalyst support, and second as a strainer. Consequently, the cylinder 28 contains minute perforations (not shown) in addition to the concrete pores.

The interior of the furnace 14 is lines with firebrick 30, and contains coiled 4 inch steel pipes 32 filled with water from line 31 for the evolution of steam from line 33. Besides the reactor, another steel cylinder 16 of the same size and thickness but without the ceramic lining (not shown) may be provided to contain the combustion gases evolved from the furnace. This steel cylinder which will contain $CO_2$ and $CO$, is lined with the ashless charcoal rammed and tamped with coal tar and baked to convert most of the $CO_2$ to $CO$. The furnace 14 is fired with oxygen to supplement atmospheric air through line 35; and the gases in this cylinder are recycled to the furnace via line 34. At the bottom of the reactor cylinder 10 is fitted the inlet 36 for hydrogen with proper inlet stop-cock valve (not shown).

The ground mixture of pure carbon, naphthalene, and mixed catalyst is charged into the hydrogenation reactor 10 just described. Hydrogen is charged into its inlet 36 and heated to about from 150°–500°C. gradually, with an increasing pressure of from 100 to 1,000 atmospheres. Samples are withdrawn from time to time to determine the extent of hydrogenation. If the sample material withdrawn is still black with some specks of unreacted charcoal, hydrogenation has to be carried on further. When hydrogenation is completed, however, the sample material is dark brownish-black and greasy to the touch. The completely hydrogenated pure carbon is then transferred via line 38 to the oxidation reactor 40, and introduced or charged at the top of the reactor in spray-jet form under pressure of about 1,000 atm. and 45° tangent to the sides of the reactor chamber.

In the hydrogenation reactor 10, the carbon is hydrogenated to form hydrocarbons, principally paraffins of $C_1$–$C_{10}$, and the naphthalene is hydrogenated to form tetrahydronaphthalene or other saturated hydrocarbons. The resulting tetralin (tetrahydronaphthalene) is an effective solvent for the purified pulverized carbon, and synergizes the rapid hydrogenation of the carbon. As tetralin is itself unsaturated it may be hydrogenated further under the high temperature and high pressure, however, the dissolved purified carbon (ashless charcoal) rapidly hydrogenates to form high molecular weight paraffinic hydrocarbons. Methane and ethane are formed at the start of the reaction, when the temperatures and pressures are still low. However, as the temperature and pressure are raised, high mol. wt. paraffinic hydrocarbons are finally formed. When the temperature is raised to 1,000°–1,500°C and the pressure to 3,000–4,000 atmospheres (which will require a stronger reactor shell) $C_{20}$–$C_{40}$ paraffins may be obtained, which are capable of producing high octane gasoline by cracking distillation.

The hydrogenated product is a suitable substitute for crude oil for diesel engines.

The oxidation reactor 40 is constructed in the same manner as the hydrogenation reactor 10. The catalyst impregnated in the ceramics lining 42 and ceramics cylinder 44 inside the steel cylinder 46 comprises 4 parts zinc oxide, 2 parts copper, 10 parts chromium oxide, 10 parts silica, 10 parts potassium oxide, and 10 parts boric oxide. The silica is first ground to fine powder, and the remaining constituents are also ground and mixed with the silica powder. The whole mixture will constitute about 20 percent of the ceramics to be made for lining 42 and for the ceramics cylinder 44. The interior cylinder 44 is also provided with minute perforations (not shown). After the proper setting of the ceramic, it is heated to 1,500°C. to activate the catalyst.

Into the oxidation reactor 40 is charged simultaneously the live steam through inlet 48 and the paraffinic hydrocarbons through inlet 50. The live steam is supplied to the bottom of the reactor 40 at 45° tangent and in the opposite direction to the flow of the hydrocarbons, in order to promote turbulent mixing. Temperature is maintained at 450°–500°C, and at the pressure of about 400–500 atmospheres the higher alcohols form, although the mixed alcohol product still may contain small amounts of methyl alcohol. The alcohols are mostly ethyl alcohol because of the selectivity of the present catalyst. The mixture of alcohols is made to pass from outlet 52 through the third reactor 54 for final and complete synthesis and condensation of residual materials.

The third reactor 54 is actually both a reactor and a distillation retort. In construction and catalyst composition, reactor 54 is similar to reactor 40, except that the interior ceramic cylinder 56 contains perforated ceramic plates 62, of the same composition, leaving ¼ inch perforations 63, in order to promote distillation of the alcohol product. The retort reactor 54 is provided with three condensers 58–60. The alcohol enters reactor 54 by inlet 57, and after the reaction is completed evolves from reactor 54 via line 64 to storage tanks 66. The higher boiling residue is removed from bottoms line 65. It is, of course, possible to remove a certain fraction at any desired point in the retort, by conventional means not shown.

The purified alcohols made by the present process may be employed in a pollution-free automotive motor fuel, in combination with hydrogen peroxide. The exhaust products of such a motor fuel are substantially carbon dioxide and water, and are hence non-polluting.

I claim:

1. A hydrogenation catalyst consisting of about 15–20 percent nickel, 15–20 percent cobalt molybdate, 15–20 percent ruthenium, and 45–55 percent aluminum deposited on a porous ceramic support.

* * * * *